US006876723B1

United States Patent
Celliers et al.

(10) Patent No.: US 6,876,723 B1
(45) Date of Patent: Apr. 5, 2005

(54) RISE TIME MEASUREMENT FOR ULTRAFAST X-RAY PULSES

(75) Inventors: Peter M. Celliers, Berkeley, CA (US); Franz A. Weber, Oakland, CA (US); Stephen J. Moon, Tracy, CA (US)

(73) Assignee: The United States of America as represented by the Department of Energy, Washington, DC (US)

( * ) Notice: Subject to any disclaimer, the term of this patent is extended or adjusted under 35 U.S.C. 154(b) by 93 days.

(21) Appl. No.: 10/613,223

(22) Filed: Jul. 1, 2003

Related U.S. Application Data

(60) Provisional application No. 60/393,688, filed on Jul. 3, 2002.

(51) Int. Cl.[7] .............................. G01N 23/00; H05G 1/64
(52) U.S. Cl. ............................. 378/87; 378/63; 378/70; 378/86; 378/98.8; 250/336.1; 250/370.09; 250/591
(58) Field of Search ............................... 378/63, 70, 76, 378/86, 90, 98.3, 98.8; 250/336.1, 370.09, 591

(56) References Cited

U.S. PATENT DOCUMENTS

| | | | |
|---|---|---|---|
| 4,215,274 A | 7/1980 | Segall | 250/361 |
| 4,873,439 A | 10/1989 | Hagelstein et al. | 250/327.2 |
| 5,617,460 A * | 4/1997 | Katayama et al. | 378/64 |
| 5,789,876 A | 8/1998 | Umstadter et al. | 315/507 |
| 6,320,367 B1 | 11/2001 | Cuzin et al. | 324/96 |
| 6,408,048 B2 * | 6/2002 | Opsal et al. | 378/89 |

* cited by examiner

Primary Examiner—Allen C. Ho
(74) Attorney, Agent, or Firm—William C. Daubenspeck; Paul A. Gottlieb

(57) ABSTRACT

A pump-probe scheme measures the rise time of ultrafast x-ray pulses. Conventional high speed x-ray diagnostics (x-ray streak cameras, PIN diodes, diamond PCD devices) do not provide sufficient time resolution to resolve rise times of x-ray pulses on the order of 50 fs or less as they are being produced by modern fast x-ray sources. Here, we are describing a pump-probe technique that can be employed to measure events where detector resolution is insufficient to resolve the event. The scheme utilizes a diamond plate as an x-ray transducer and a p-polarized probe beam.

20 Claims, 10 Drawing Sheets

RISE TIME MEASUREMENT FOR ULTRAFAST X-RAY PULSES

This application claims priority to Provisional Patent Application Ser. No. 60/393,688, titled "Rise Time Measurement For Ultrafast X-Ray Pulses," filed Jul. 3, 2002, incorporated herein by reference.

The United States Government has rights in this invention pursuant to Contract No. W-7405-ENG-48 between the United States Department of Energy and the University of California for the operation of Lawrence Livermore National Laboratory.

BACKGROUND OF THE INVENTION

1. Field of the Invention

The present invention relates to techniques for characterizing the pulse profile of a fast x-ray source, and more specifically, it relates to a pump-probe technique for measuring the rise time of a fast x-ray pulse.

2. Description of Related Art

Conventional high speed x-ray diagnostics (e.g., x-ray streak cameras, PIN diodes, diamond PCD devices) do not provide sufficient time resolution in order to resolve x-ray pulses having a duration that is less than about 1 ps. For optimization and study of ultrafast systems in general, it is important to have this capability developed.

Measurements of very short-duration x-ray pulses have been made using very fast photodetectors, which can resolve events as short as 50 ps, and with x-ray streak cameras which can resolve events as short as 1 ps. A typical x-ray streak camera provides a continuous exposure for a very short time interval and achieves good time resolution by rapidly changing the position, or streaking, the image on the recording surface, which may be film or a phosphor screen. The image is rapidly moved over the recording surface by using either a rapidly rotating mirror or deflection plates. X-ray streak cameras have been previously used for measurement of light or x-ray fluxes of relatively large magnitude. For x-ray measurements of large flux magnitude, the x-rays are collimated through a small slit. It is desirable to provide a pump-probe solution to measuring events where detector resolution is insufficient to resolve the event. The present invention provide such techniques.

SUMMARY OF THE INVENTION

It is an object of the present invention to provide pump-probe techniques for measuring the rise time of x-rays pulses on the order of 20 fs or less.

This and other objects will be apparent to those skilled in the art based on the teachings herein.

The pump-probe scheme described in this disclosure is depicted in FIG. 1. X-ray energy from the fast source impinging on the surface of the diamond plate will photo-ionize near-surface atoms by ejecting electrons from inner-shell states and create a transient population of free carriers in the conduction band. These carriers will recombine rapidly through Auger recombination processes. However, calculations show that the transient carrier density will be high enough to modify the optical reflectivity of the interface such that it can be detected by the probe beam. The arrangement employs a p-polarized probe beam entering the diamond plate at Brewster's angle. As is shown in FIG. 2, with no x-ray interaction the nominal reflectivity at Brewster's angle is zero, and no signal should be registered on the detector. If the probe beam arrives at the sample simultaneously with the pump, the surface reflectivity will be modified by the presence of the x-ray-generated free carriers and a stronger reflection can be observed at the interface.

The arrangement encodes time-related information spatially because the probe beam interacts obliquely with the x-ray transducer. This encodes a linear gradient of arrival times across the sample, which can be extracted by imaging the reflected beam onto a CCD detector array. By placing the x-ray transducer at a moderate angle relative to the sample, additional adjustments can be made in the time-to-space encoding. Utilization of a diamond plate provides increased sensitivity of the measurement around the carbon K absorption edge, which is an important region of x-ray emission spectra in a variety of applications.

The physical mechanisms of the pump-probe experiment have been theoretically analyzed by treating the transient electron population as a free electron gas employing the Drude model. The fast x-ray source preferentially releases K-shell electrons into the conduction band. In addition to the photoelectrons there are also Auger electrons, which, through collisions, result in a cascade of electrons into the conduction band. The near surface accumulation of electrons changes the index of refraction, n, and subsequently the reflectivity increases from nominal zero to a detectable level as is shown below. The photo production rate yielding photoelectrons as a result of x-ray source impact is given by, $$R_{photo} = \int dE \sigma_{photo} \Phi(E)$$

where $\sigma_{photo}$ is the photo-ionization cross-section and $\Phi(E)$ is the incident x-ray flux. The photoelectrons populate the conduction band and additional Auger electrons create further conduction electrons through collisional ionization. Here the rate is given by, $$R_{electron} = \int dE \sigma_{electron} N_e(E) v(E)$$

where $\sigma_{electron}$ is the electro-ionization cross-section and $v$ is the electron velocity and $N_e(E)$ is the number of electrons per unit volume. This ionization creates a transient population in the conduction band. Assuming a Drude model, the dielectric function is given by, $$\varepsilon(\omega) = \varepsilon_0 - \frac{\omega_p^2}{\omega(\omega - i/\tau)}$$

where $$\omega_p = \left(4\pi \frac{N_e e^2}{m}\right)^{1/2}$$

is the plasma frequency, $N_e$ is the free electron density, $\tau$ the electronic relaxation time, $\epsilon_0 = n_0^2$ is the inter-band contribution to the dielectic constant, m is the reduced mass, and $n_0$ is the index of refraction of diamond. The modified index of refraction, $$n = \sqrt{\epsilon}$$

is dependent on the electron density and changes corresponding to the time history in FIG. 3. When the electron density is zero, one has $n = \sqrt{\epsilon_0} = n_0$. The optical reflectivity $R = f(Re(n), Im(n))$ at the interface is modified and the probe beam at Brewster's angle will yield a non-zero reflected signal on the time scale indicated in FIG. 4.

DETAILED DESCRIPTION OF THE INVENTION

Principle of Operation: X-Ray Modulation of p-Polarized Reflectivity

Figure 1:
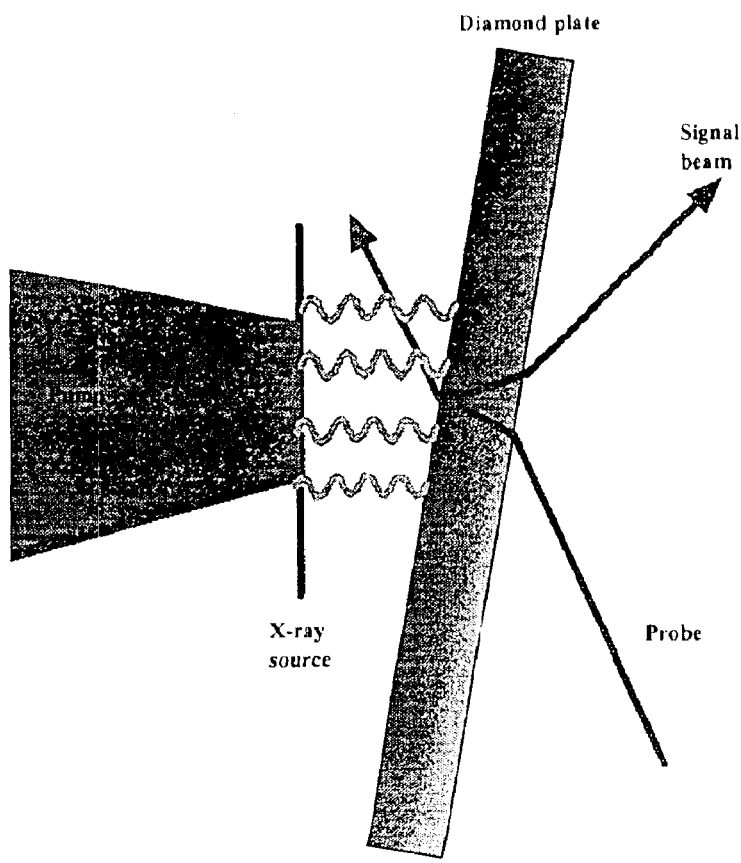
FIG. 1 is a schematic of an embodiment of the present invention for time-resolved measurements of x-ray emission.
Figure 2:
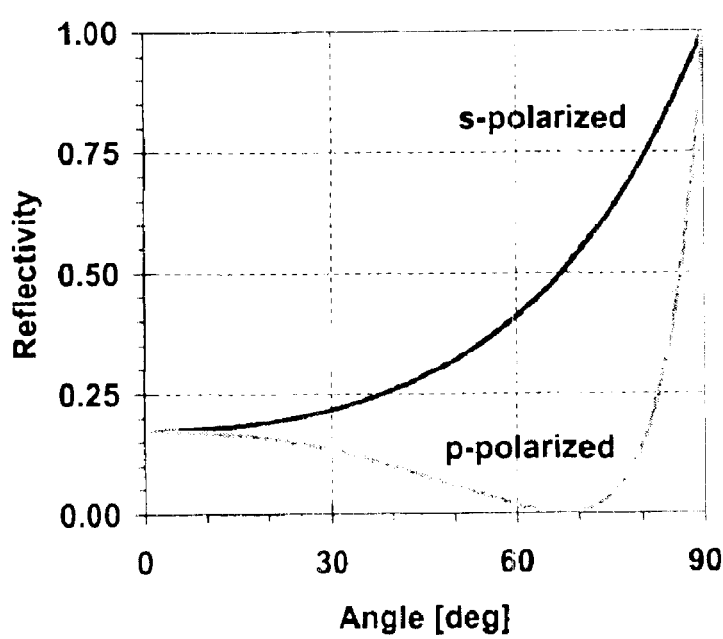
FIG. 2 shows the optical reflectivity function for diamond.
Figure 3:
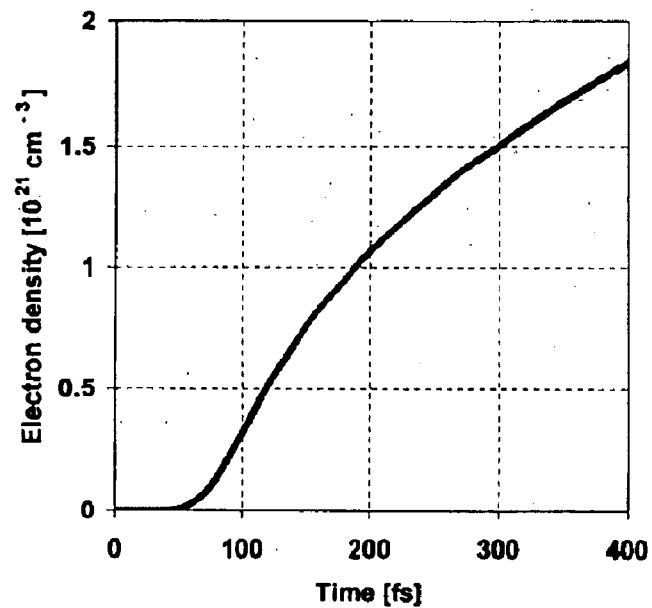
FIG. 3 shows the transient conduction band population in diamond x-ray transducer.
Figure 4:
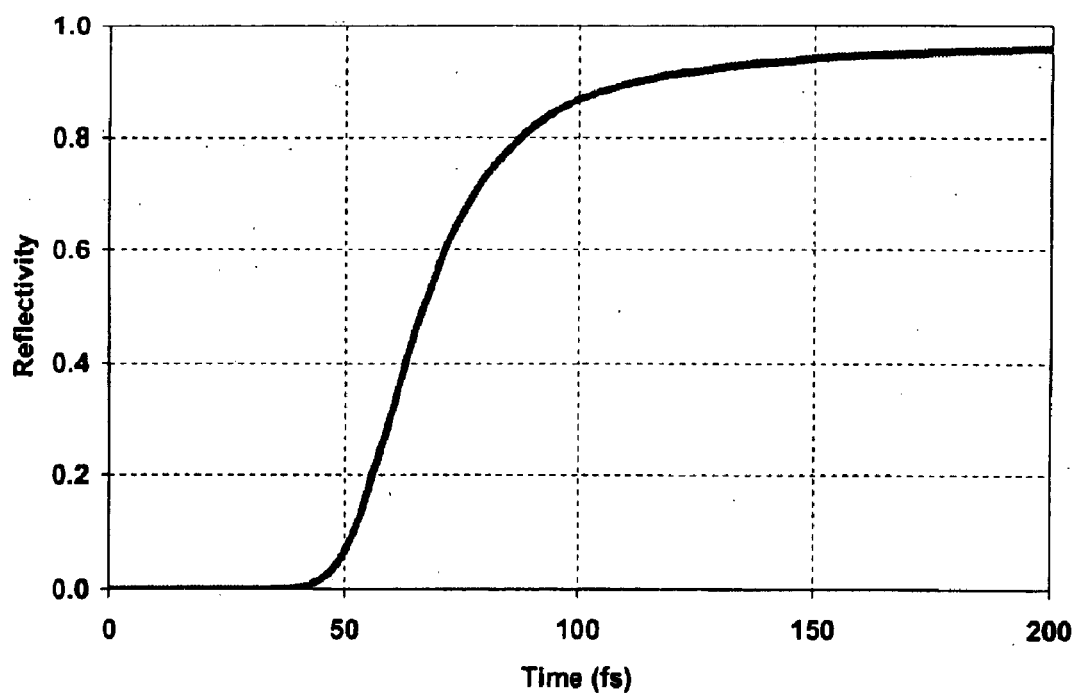
FIG. 4 shows dynamic response of interface reflectivity.
Figure 5:
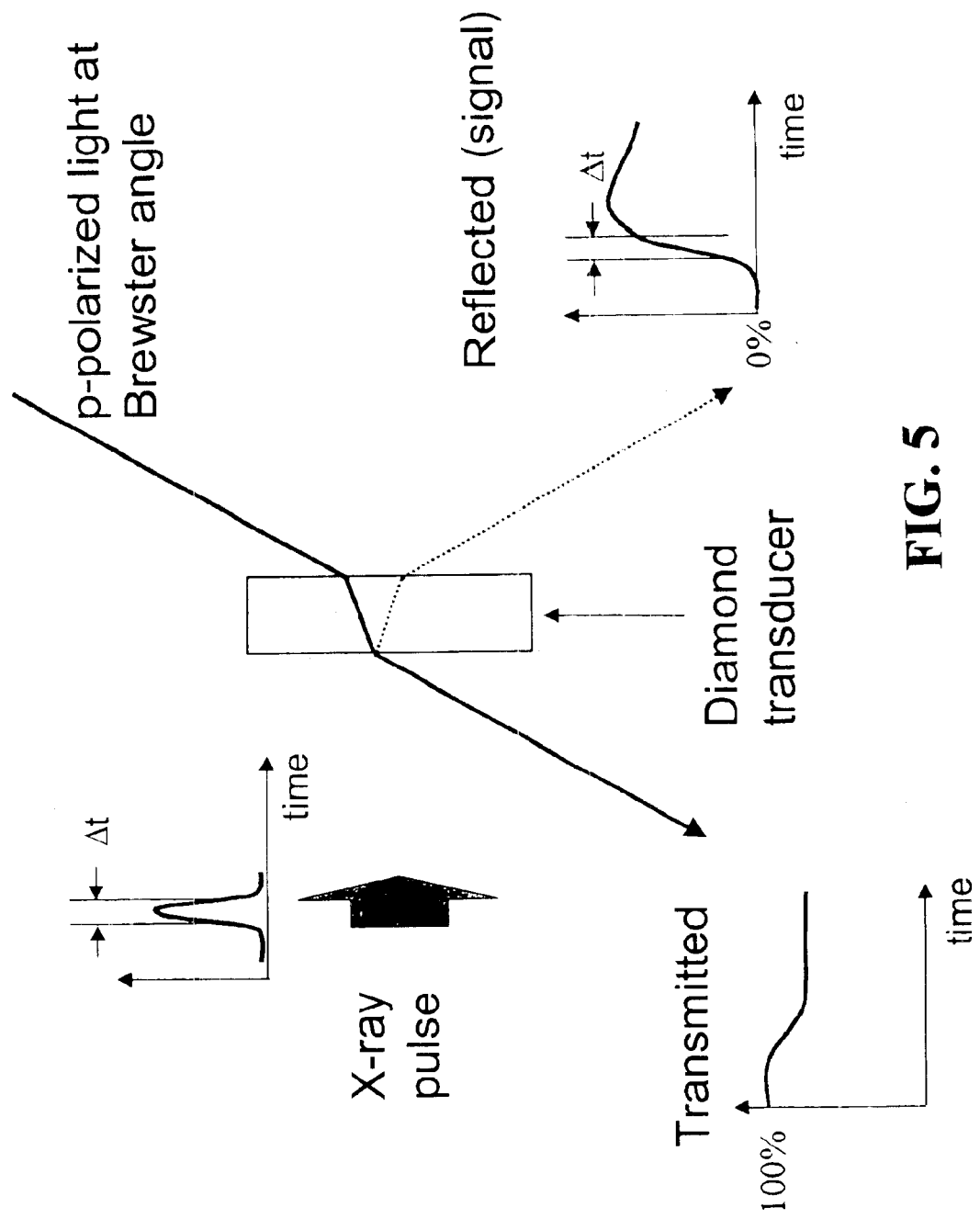
FIG. 5 is a sketch of an embodiment of the measurement geometry.

The rise time measurement employs a diamond transducer in which x-rays from the source are used to modulate the reflectivity of the crystal for p-polarized light. (Diamond was chosen for the particular needs of the experiment; however, other dielectric crystals, e.g., z-cut alpha quartz ($SiO_2$) or z-cut sapphire ($Al_2O_3$), could equally well be used. The modulated reflectivity of the diamond transducer has to be probed with a short duration pulse of light in order to produce a time-resolved interrogation of the surface p-polarized reflectivity of the transducer. A sketch of the measurement geometry is shown in FIG. 5.

The transmission of p-polarized light at the Brewster angle is 100% for transparent dielectric materials that have real-valued index of refraction (imaginary part of the index= 0); this is well known from optics. Therefore there should be 0% reflection from the diamond transducer when the beam is p-polarized and arranged precisely at the Brewster angle, and there are no x-rays impinging on the transducer.

The Brewster angle reflectivity is not zero if the index of refraction takes on a non-zero imaginary part of the index of refraction. Any mechanism that modifies the index of refraction of the diamond at the reflecting surface will induce a non-zero p-polarized Brewster angle reflectivity at that surface. When x-rays are absorbed in the crystal, they eject electrons from the K-shell into the electronic conduction band of the crystal. The presence of a large population of conduction electrons will result in a non-zero imaginary part of the index of refraction, and therefore result in a non-zero p-polarized reflectivity. The inner-shell ionization of K-shell electrons into the conduction band is a prompt process— there is no time delay between the absorption of the photon and the change of state of the electron. The magnitude of the reflectivity change is related to the intensity of the x-ray pulse.

The diamond plate acts as a transducer to convert a time-varying x-ray pulse into a time-varying optical pulse. If a p-polarized beam is shined on the crystal and a detector is placed, such as a fast photodiode or a streak camera, to intercept the reflected beam, then one could record the time history of the reflected light to obtain a measure of the rise time of the x-ray flux impinging on the crystal. However, such a measurement would not be able to discriminate against x-ray pulse shorter than about 50 ps if the detector were a fast photodiode, or about 1 ps if the detector were a fast streak camera. The current state of the art for time resolving events with an x-ray streak camera is limited to about 500 fs. This limit i a factor of 10–20 times longer than the events it is desirable to resolve. To measure the time-history of an event shorter than 500 fs requires a pump-probe method, described below.

Pump Probe Method

Figure 6:
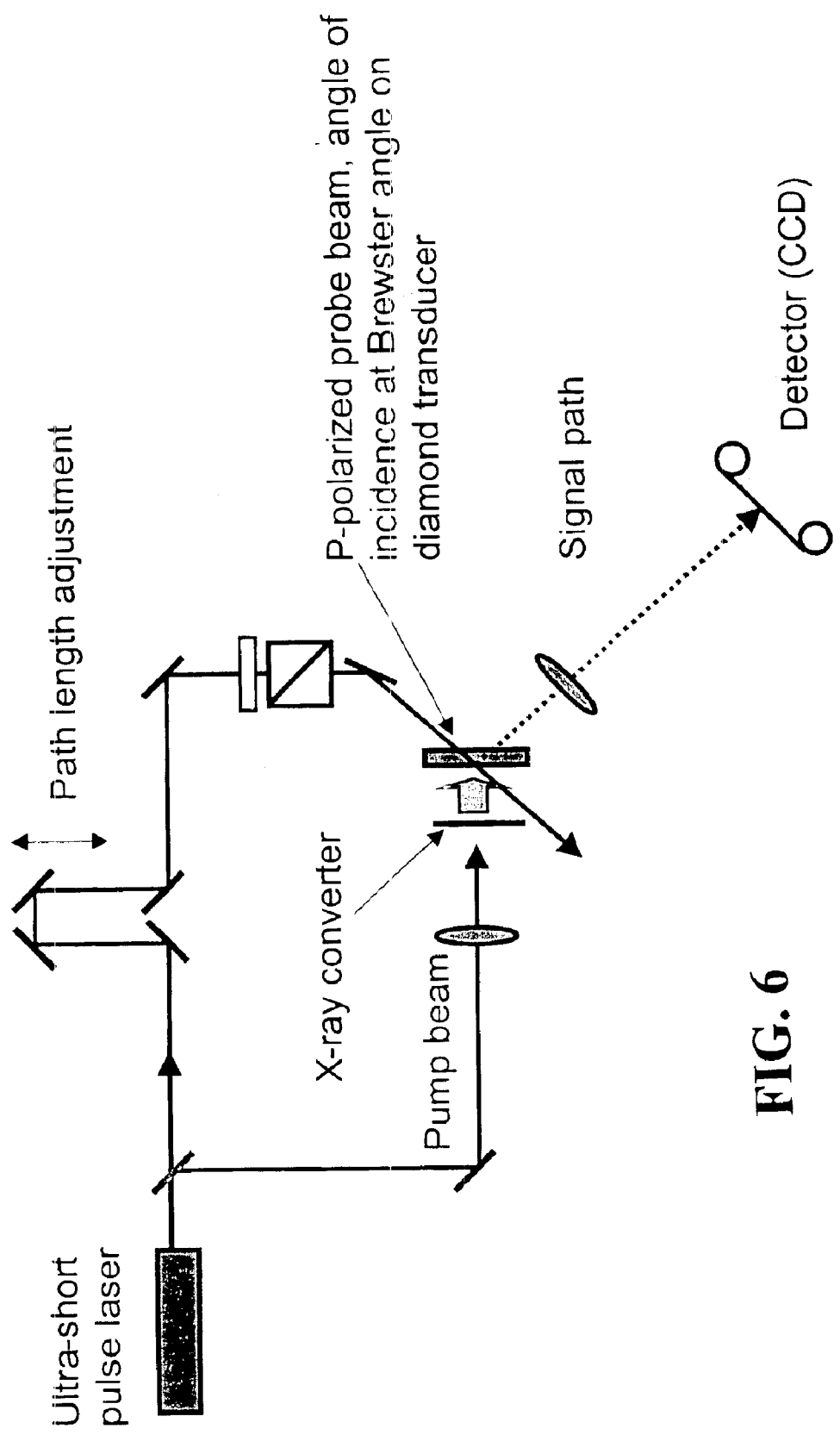
FIG. 6 is an overview of an embodiment of the measurement system.

An overview of the measurement system is shown in FIG. 6. A high-energy ultra-short pulse laser produces the short x-ray pulse. This is accomplished by focusing the short pulse beam onto a thin x-ray converter foil using an off-axis parabolic mirror (shown figuratively as a lens in FIG. 6). A small portion of the ultra-short laser beam is split off from the main beam pulse to be used as a probe pulse. This beam is routed through a separate and independent path to arrive at the rear side of the x-ray converter. The path length of this arrangement must match that of the pump pulse to within a few microns in order to ensure simultaneity of arrival with the x-ray pulse. Precise synchronization is enabled by using a path delay adjustment (delay trombone) in this path.

Figure 7:
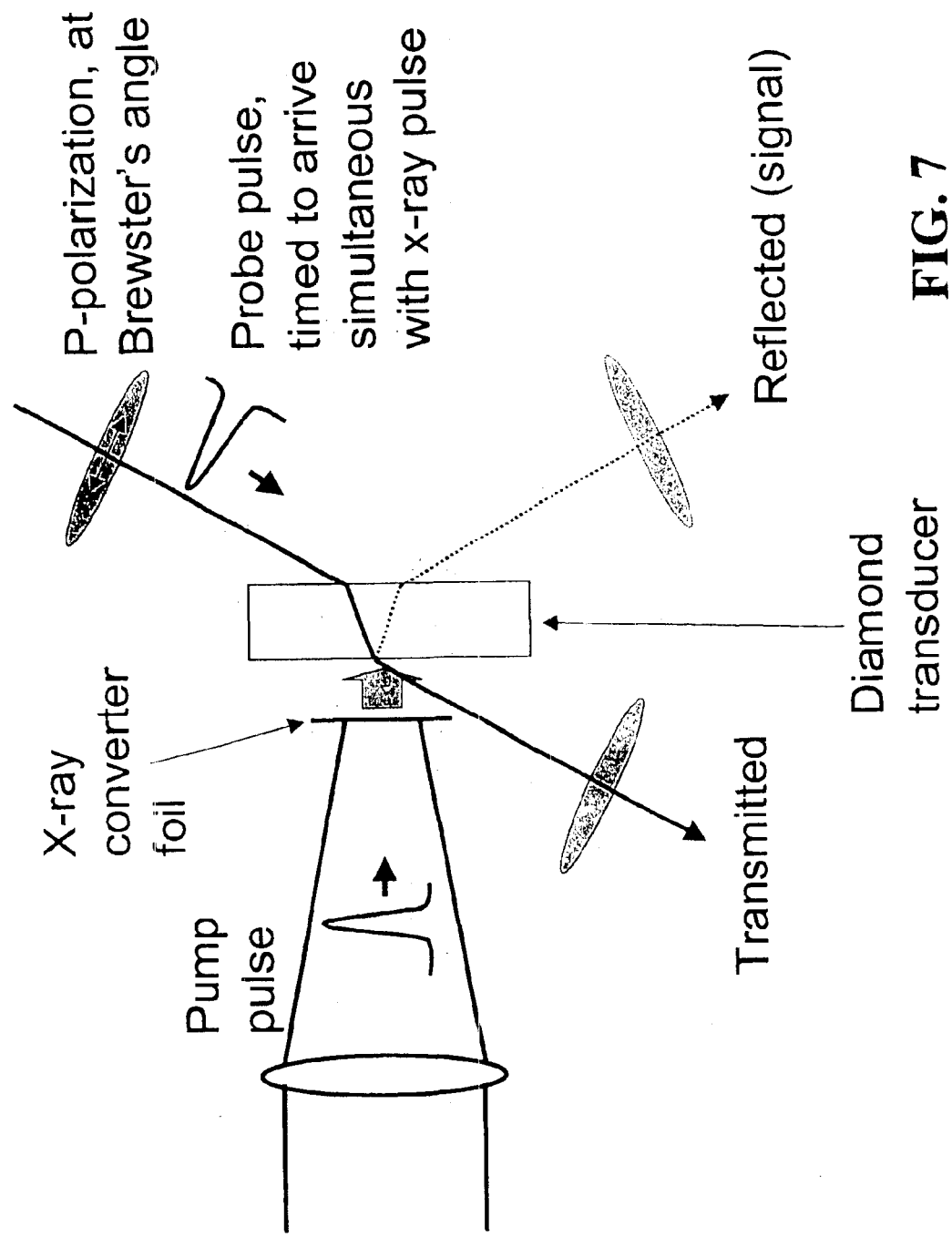
FIG. 7 illustrates several conditions of the probe beam.

FIG. 7 illustrates several conditions required of the probe beam. (1) Polarizing elements must render the probe beam to be precisely in the p-polarized state when it arrives at the transducer (i.e., the s-polarized component must be removed). (2) Optics must format the beam such that it is collimated with a diameter of approximately 1 mm–3 mm, and such that the beam is spatially uniform in intensity when it enters the diamond crystal. (3) Its angle must be controlled precisely such that it is incident on the transducer at precisely the Brewster angle for diamond. The Brewster angle is given by tan (theta_Brewster)=n_diamond, where n_diamond is the refractive index of diamond. n_diamond=2.400, and theta_Brewster=67.4 degrees. When the probe beam enters the crystal, it is refracted such that its propagation direction inside the crystal is different from the exterior direction. The interior angle of the probe beam, theta_t, is given by Snell's law, sin(theta_t)=n sin(theta_Brewster), which for diamond is theta_t=22.6 degrees.

Figure 8:
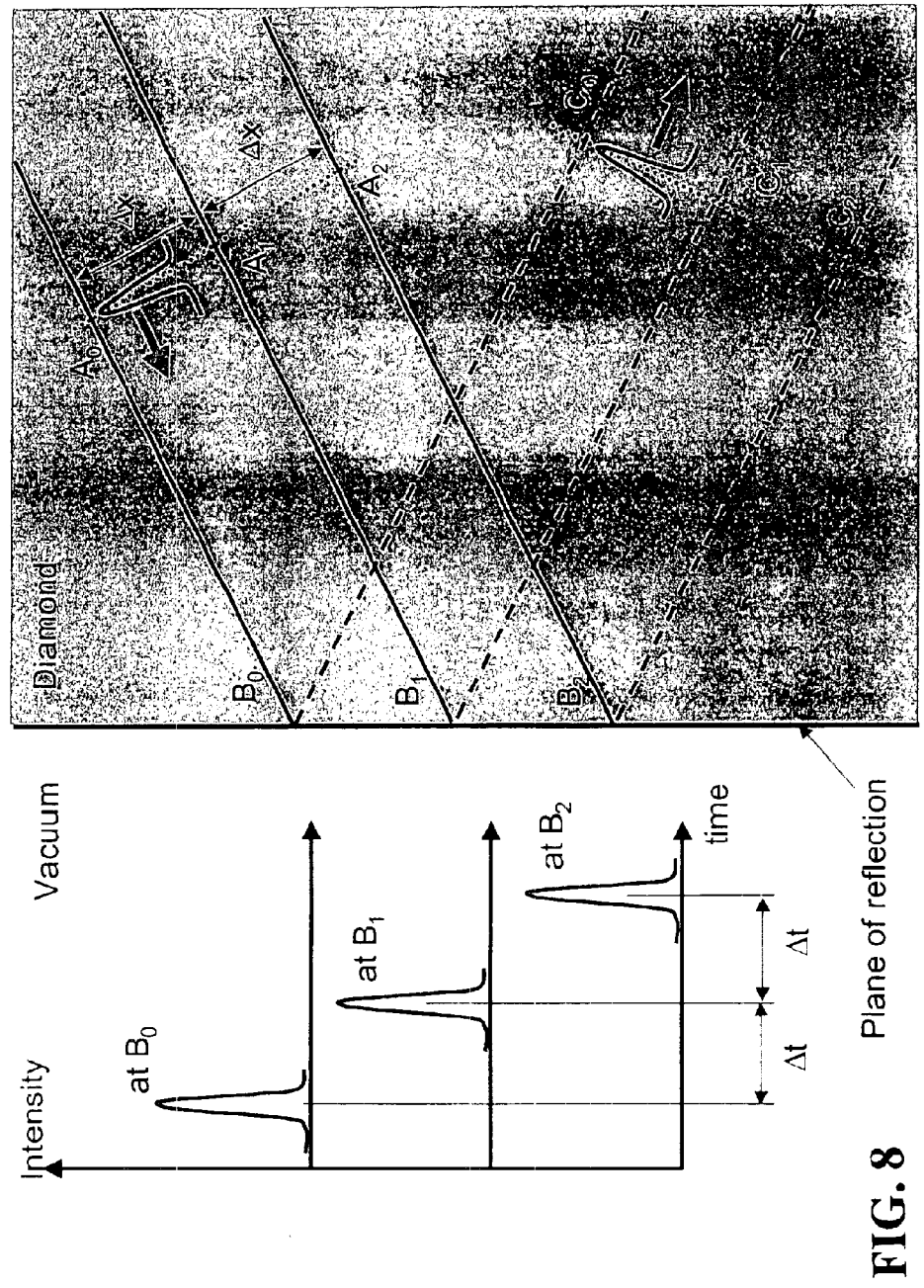
FIG. 8 follows the probe beam in the crystal through its interaction with the rear surface and back out upon reflection.

FIG. 8 follows the beam in the crystal through its interaction with the rear surface and back out upon reflection. In particular, consider the interaction of three (3) specific locations of the beam, the right edge, A0, middle, A1 and left edge A2; each of these rays is spatially separated from its neighbor by distance delta-x. These parts of the beam reflect from the crystal rear surface at B0, B1 and B2 respectively such that the reflected rays corresponding to these points are at C0, C1 and C2 respectively. Each of these rays interacts with the crystal surface at different times according to the geometry of the ray angles.

Figure 9:
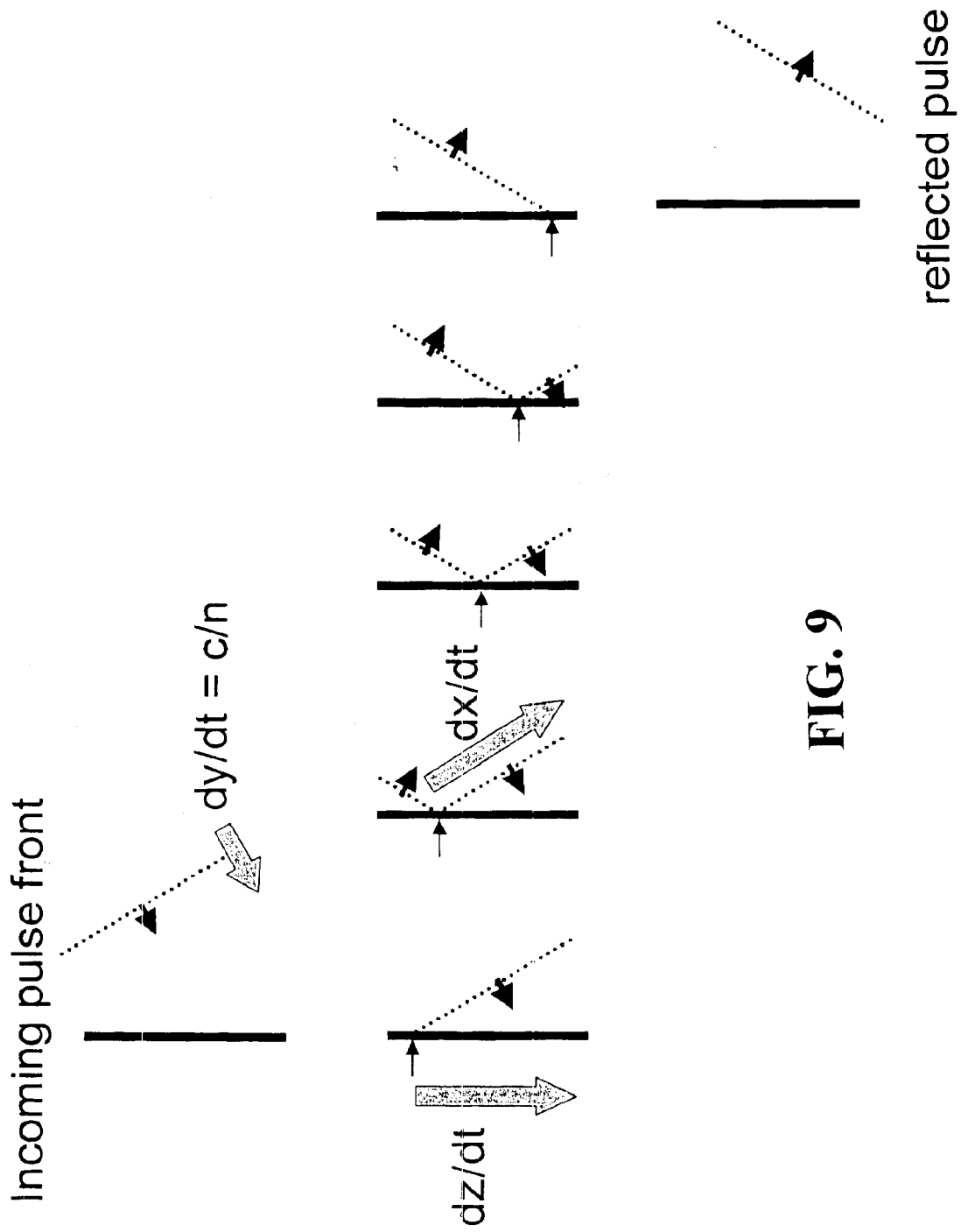
FIG. 9 illustrates the case of an ultra-short pulse of 40 fs duration traveling through the crystal.

FIG. 9 illustrates the case where the ultra-short pulse of tau=40 fs duration traveling through the crystal is a wave packet of electromagnetic energy that encompasses a spatial extent of 1–3 mm in diameter, and about 5 μm thickness (thickness=(c/n) tau, where c is the speed of light in vacuum, n is the index of refraction, and (c/n) is the speed of light in the crystal). Note that the "thickness" of the pulse is much less than its diameter. In spatial configuration it is similar in spatial extent to a pancake-shaped bundle of electromagnetic energy that travels along a path that is perpendicular to the surfaces of the pancake.

There is a precise relationship between the arrival time history of parts of the the pulse front carried along these rays and their relative spatial separation. Let the z-axis be fixed along the crystal surface in the plane of incidence and along the crystal surface. The x-axis is also in the plane of incidence and parallel to plane of the pulse front. The y-axis is in the plane of incidence and parallel to the ray direction, therefore perpendicular to the x-axis. The pulse arrives and reflects from the crystal surface along a line perpendicular to the plane of incidence; in the figures these lines are perpendicular to the page, and appear as points: B0, B1, and B2 etc. As the pulse begins it interacts with any of the points B0, B1, B2 for only the short duration of the pulse. This point of interaction moves along the crystal surface (from B0, to B1 to B2 etc) at a rate dz/dt. In particular, if the ray A0 arrives at time t0, the ray A1 at time t1=t0+delta-t and A2 at t2=t1+delta-t=t0+2 delta-t. Although the pulse itself is very short, 40 fs, its total time of interaction is much longer: i.e., from the time when the left edge of the pulse intersects the plane of reflection and to the time when the right edge of the reflected pulse leaves that plane is given by D/c, where D is the diameter of the pulse and c is the vacuum speed of light. For a 3 run diameter beam this is 10 ps, about 200 times longer than the pulse itself. If the reflectivity of the reflection plane is changing in time, then the amount of reflected energy carried along each ray element will change as the reflection process progresses, leading to the result that the time variation of the reflectivity is imprinted on the beam as a spatial variation in beam intensity.

Figure 10:
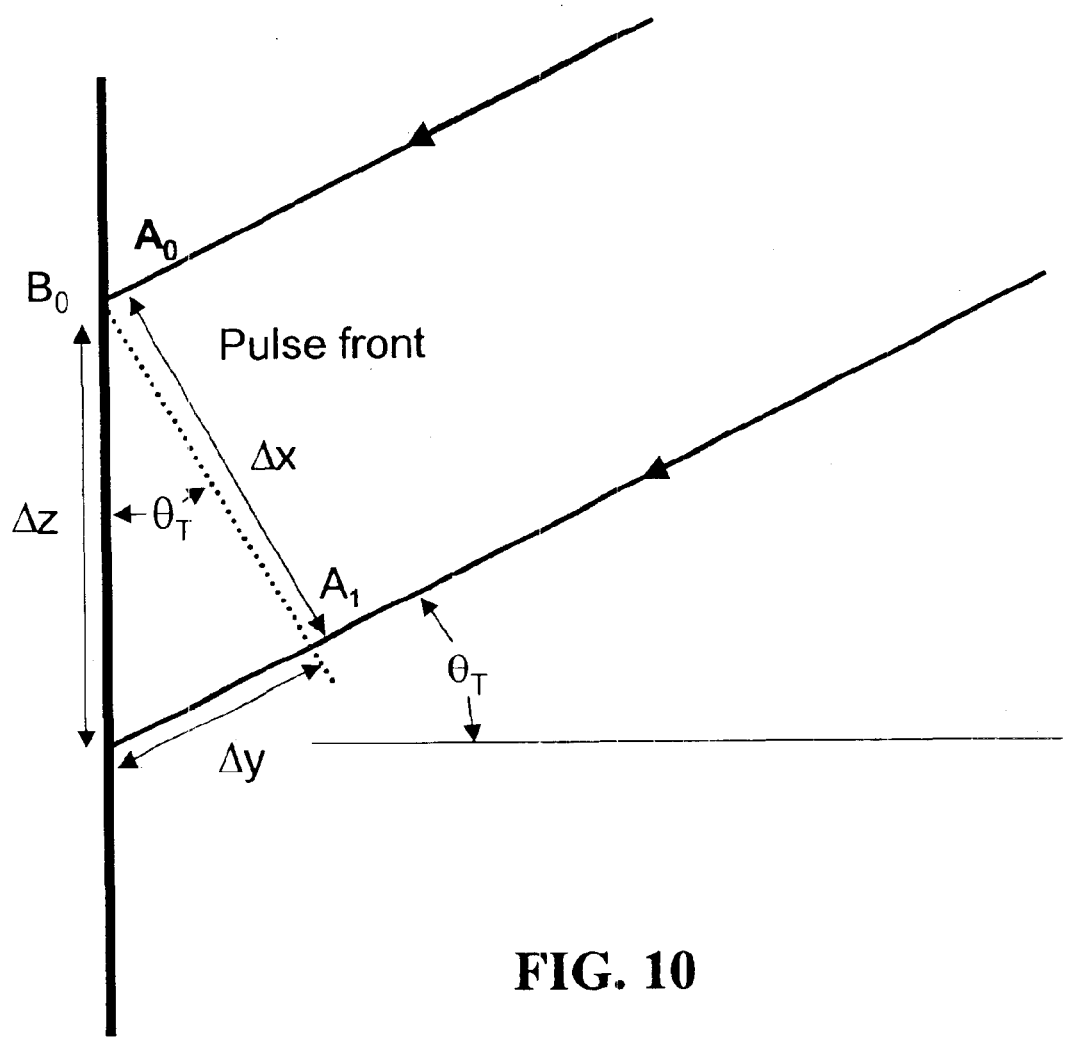
FIG. 10 shows the relationship between the beam geometry and pulse intersection rates.

FIG. 10 shows the relationship between the beam geometry and pulse intersection rates. During time interval delta-t, the pulse packet travels distance delta-y=(c/n) delta-t. The intersection of the pulse with the reflection occurs at the points B (e.g., B0, B1, B2), which move along the plane at rate dz/dt. Similarly the intersection point moves at rate dx/dt relative to the plane of the pulse. These three rates are related to each other through the beam geometry. In particular since tan(theta_t)=delta-y/delta-x, it can be shown that dx/dt=(dy/dt)/(tan(theta-t))=(c/n)/tan(theta-t)=c, where c is the vacuum speed of light. This result holds for the special case of the Brewster angle geometry for any transparent dielectric transducer material. Similarly it is evident from the geometry that dz/dt=(dx/dt)/cos(theta-t). In the case of diamond, this velocity is 1.08 c in the Brewster geometry; it would be a different number for another material.

Figure 11:
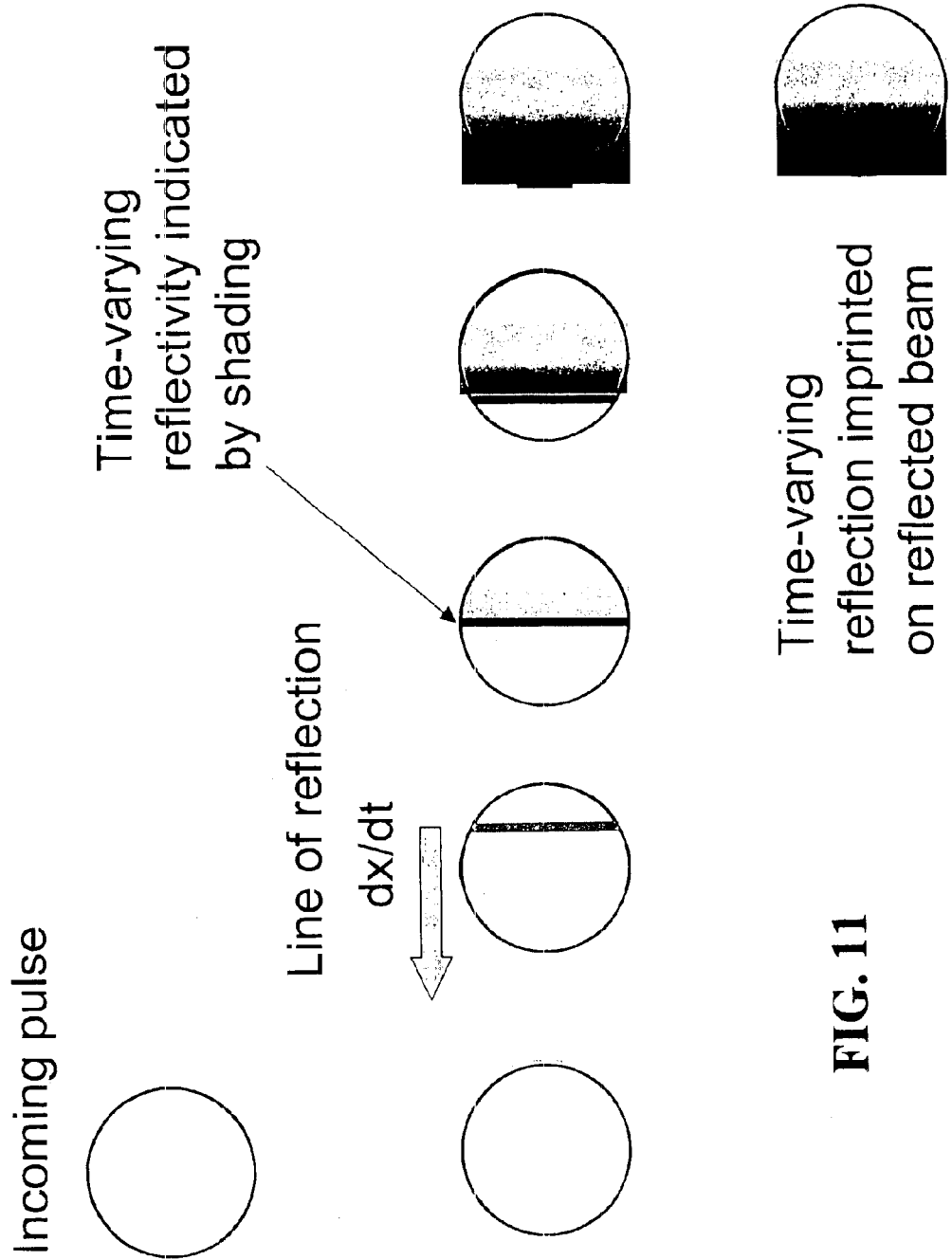
FIG. 11 shows the measurement of time varying reflectivity imprinted into the beam itself.

FIG. 11 shows the measurement of time varying reflectivity is imprinted into the beam itself, so the rate dx/dt provides a precise mapping between the spatial variation of the beam intensity and the temporal variation of its interaction with the transducer. Since dx/dt=c=0.3 µm/fs, one can map the spatial scale of the beam to a time axis, dt/dx=1/c=3.3 fs/µm, or 3.3 ps/mm. Thus for a 1 mm beam, a 3.3 ps time window is sampled during the interaction of the pulse with the reflection plane; for a 3 mm beam, a 10 ps time window is sampled. The probe pulse duration limits the resolving time of the interaction, since the probe interacts with the reflection surface for a finite time, and is spread out over a finite spatial extent over the surface by an amount proportional to this duration. A pulse duration of 40 fs corresponds to a spatial extent of δx=40 fs*dx/dt=12 µm. This gives size of the smallest spatial feature that will be imprinted on the beam using this technique with a probe pulse of 40 fs duration. For a 1 mm beam of 40 fs duration, the total number of resolution elements is given by D/δx=83. For a 3 mm diameter beam one has 250 resolution elements over the longer time window.

To extract the data from the beam, one must form an image of the intensity pattern imprinted on the beam at the reflection plane. This is done by using a high quality microscope objective or camera lens to form a magnified image of the beam onto a film or CCD camera detector. The magnification must be well known and calibrated in order to preserve the spatial-to-temporal mapping relationship. As an example one could use a scientific grade CCD with 1024× 1024 pixel elements (25×25 mm active area), coupled with a 50 mm camera lens at magnification 10× to map a 2 mm probe beam onto a 20 mm diameter area of the CCD. Each 25 µm pixel corresponds to a 2.5 µm part of the beam, or about 0.2 of a resolution element for a 40 fs probe pulse (i.e., 8 fs). The total time window viewable in this spatial mapping would be 20 mm/10/c=6.7 ps.

The time-varying reflectivity information is imprinted on both the transmitted and reflected beams. In the case of the transmitted beam the intensity will decrease as the surface reflectivity increases so the signal will show a reduction of transmitted intensity for increasing signal. The reflected beam is reversed from this, because the p-polarized reflectivity is initially zero. The reason to use the reflected beam is that the initially zero reflectivity level allows signal collection to occur over a very wide dynamic range. Thus x-ray-induced reflectivity of only a few percent or less may be easily detectable. In practical terms it is possible to extinguish the initial reflectivity by an amount related to the p-versus s-polarization extinction ratio achievable with the polarizing optics, and the degree to which the incident beam can be matched to the Brewster angle. This should be possible down to levels as low as 0.001 or 0.0001 (1000:1 to 10000:1 extinction ratio). A measured peak reflectivity of 0.1 would be 100×–1000× stronger than the baseline, thus providing a dynamic range of 2 to 3 orders of magnitude.

Connection Between the Surface Reflectivity and Electron Density Near the Reflection Plane The Brewster reflectivity of the reflecting plane is modified when the absorption of x-rays at the surface excites electrons into the conduction band of the crystal. When this happens the imaginary part of the refractive index of the crystal becomes non-zero. An expression relating the dielectric function of the crystal to the density of conduction band electrons (carrier density) is $$\epsilon = n_0^2 - (\omega_p/\omega)^2 (1+i/\omega\tau)^{-1}$$

where $\omega_p^2 = 4\pi n_e/m$ where $\epsilon$ is the frequency dependent dielectric function, $n_0$ is the index of refraction of the crystal, $n_e$ is the density of carrier electrons, m is the reduced mass of the electrons in the conduction band, $\omega_p$ is a plasma frequency associated with the carrier electron density and $\tau$ is a relaxation time associated with electron scattering. This is the well-known Drude description of the dielectric function of a conducting medium (see Max Born & Emil Wolf, "Principles of Optics", 6$^{th}$ edition, Pergamon Press, Oxford, 1980, section 13.3, p. 624). For diamond $n_d$=2.4, and the relaxation time is $\tau$=1 ps or longer (its exact value over does not affect the reflectivity significantly). The index of refraction of the modified (x-irradiated) material with finite electron density $n_e$ is given by $n^*(n_e)$=sqrt($\epsilon(n_e)$).

The surface reflectivity at the Brewster angle is given by (see Born&Wolf, "Principles of Optics", 6$^{th}$ edition, section 1.5.2 & 1.5.3, p. 40), $$R_B = \left| \frac{\cos\theta_T - n * \cos\theta_{Brewster}}{\cos\theta_T + n * \cos\theta_{Brewster}} \right|^2$$

Figure 12:
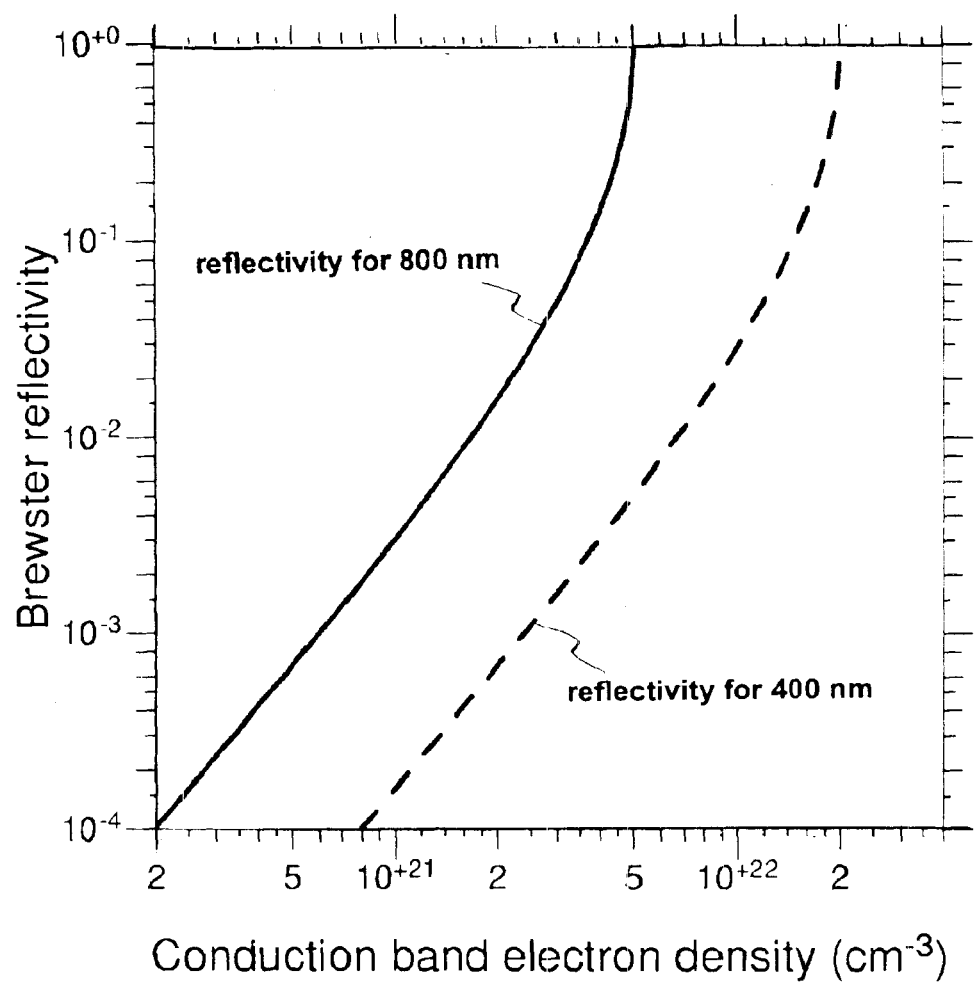
FIG. 12 shows the relationship between the Brewster reflectivity and the carrier density.

Using this formula one can verify that when $n_e \to 0$, $n^* \to n_d$ and $R_p \to 0$. For non-zero $n_e$ there is a finite Brewster reflectivity. The relationship between the Brewster reflectivity and the carrier density is shown in FIG. 12. This shows that the Brewster reflectivity varies as the square of $n_e$ up to a maximum $n_e$, above which the reflectivity saturates at unity. The maximum $n_e$ varies inversely as the square of the probe laser wavelength, and can be adjusted by changing the wavelength of the probe laser. For example by adding a frequency doubling crystal to the probe beam path one can produce a 400 nm frequency-doubled probe beam from the 800 nm fundamental. Using this probe will produce a shifted reflectivity curve.

Connection Between the X-ray Source and $n_e$

The free electrons in the conduction band are generated by irradiation of the sample surface with a short intense pulse of x-rays with photon energies near the binding energy of the inner shell (K-shell) electrons of carbon, about 300 eV. As can be seen from FIG. 11, electron densities ranging from 1e20 to 1e22 $cm^{-3}$ are needed to produce a measurable reflectivity (R>=0.0001).

The x-ray converter foils convert a few percent of the incident pump laser energy into soft x-rays near Eph=300 eV (assume a conversion efficiency X=0.01 (i.e., 1%)). As an example of the feasibility of producing a measurable signal (i.e., producing electron densities around 1e21 near the surface of the crystal), consider a 40 fs pulse containing E=100 mJ of energy focused to a spot diameter of Dspot=100 microns. The total number of x-ray photons produced per unit area is, $$Phi = E*X*(4/pi/Dspot^2)/Eph = 2.6e17 \text{ photons}/cm^2$$

Photons with energy just below the K-absorption edge are absorbed in the diamond within an e-folding absorption length of about Dabs=0.7 microns, while photons with energy just above the K-absorption edge are absorbed with e-folding length about 0.1 micron. (The K-absorption edge for diamond is about 280 eV.) An average absorption depth is about Dabs=0.4 microns. Thus the total x-ray flux of 2.6e17 photons/$cm^2$ are absorbed at an average volumetric density of Phi/Dabs=2.6e17/(0.4×1e-4 cm)=6.5e21 photons/$cm^3$. Each photon produces about 1 electron (there is a difference above and below the edge), so the x-ray source will produce an electron density of about 6.5e21 per $cm^3$. This is enough to produce 1% Brewster reflectivity at 400 nm and 100% Brewster reflectivity at 800 nm. This reflectivity will not appear instantaneously, but will rise up over the duration of the x-ray pulse, since the rate of production of free electrons depends on the time dependence of the arrival of x-rays at the crystal surface. The time-resolving capabilities of the rise-time measurement invention, described above, will allow determination of the rise time of the x-ray pulse.

Additional detail for the invention—use of 400 nm and 800 nm simultaneously will extend the dynamic range. One can produce the two probes using a doubling crystal on the probe path, then separate the two wavelengths on the reflection side with a dichroic mirror.

The foregoing description of the invention has been presented for purposes of illustration and description and is not intended to be exhaustive or to limit the invention to the precise form disclosed. Many modifications and variations are possible in light of the above teaching. The embodiments were chosen and described to best explain the principles of the invention and its practical application to thereby enable others skilled in the art to best use the invention in various embodiments and with various modifications suited to the particular use contemplated. The scope of the invention is to be defined by the following claims.

We claim:

1. A method for measuring the rise time of an x-ray pulse, comprising:

providing a dielectric material that has a material property of having zero effective reflectance at a wavelength $\lambda_1$ directed onto said dielectric material;

directing an x-ray pulse onto an area of said dielectric material to produce a reflectivity change in said dielectric material, wherein said x-ray pulse has sufficient energy to alter the reflectivity of said dielectric material at said wavelength $\lambda_1$, wherein said reflectivity changes from a minimum to a maximum;

directing a polarized probe beam at wavelength $\lambda_1$ onto said area of said dielectric material as said reflectivity changes to produce a reflected beam, wherein said reflected beam will be reflected at an intensity that is a function of said reflectivity change over time; and detecting and recording the intensity change as a function of time, wherein said intensity change as a function of time corresponds to the rise time of said x-ray pulse.

2. The method of claim 1, wherein said wavelength $\lambda_1$ is directed at Brewster's angle of incidence onto said dielectric material at p-polarization, wherein said x-ray pulse has sufficient energy to alter the Brewster's angle reflectivity of said dielectric material at said wavelength $\lambda_1$, wherein said p-polarized probe beam is directed at said wavelength $\lambda_1$ at Brewster's angle of incidence onto said area of said dielectric material as said reflectivity changes to produce said reflected beam.

3. The method of claim 1, wherein said dielectric material comprises a diamond plate.

4. The method of claim 1, further comprising encoding time-related information spatially onto said probe beam.

5. The method of claim 1, further comprising encoding a linear gradient of arrival times on said probe beam by orienting said dielectric material at an angle relative to said x-ray pulse.

6. The method of claim 1, wherein the step of detecting comprises imaging said reflected beam onto a CCD detector array.

7. The method of claim 1, wherein the step of detecting comprises imaging said reflected beam onto a film.

8. The method of claim 1, wherein said dielectric material is selected from the group consisting of z-cut alpha quartz ($SiO_2$) and z-cut sapphire ($Al_2O_3$).

9. The method of claim 1, wherein time-varying reflectivity information is imprinted on both the transmitted and reflected beams.

10. The method of claim 1, wherein said dielectric crystal comprises an antireflection coating.

11. An apparatus for measuring the rise time of an x-ray pulse, comprising:

a dielectric material that has a material property of having zero effective reflectance at a wavelength $\lambda_1$ directed onto said dielectric material;

means for directing an x-ray pulse onto an area of said dielectric material to produce a reflectivity change in said dielectric material, wherein said x-ray pulse has sufficient energy to alter the reflectivity of said dielectric material at said wavelength $\lambda_1$, wherein said reflectivity changes from a minimum to a maximum;

means for directing a polarized probe beam at wavelength $\lambda_1$ onto said area of said dielectric material as said reflectivity changes to produce a reflected beam, wherein said reflected beam will be reflected at an intensity that is a function of said reflectivity change over time; and means for detecting and recording the intensity change as a function of time, wherein said intensity change as a function of time corresponds to the rise time of said x-ray pulse.

12. The apparatus of claim 11, wherein said means for directing a polarized probe beam is adapted to direct wavelength $\lambda_1$ at Brewster's angle of incidence onto said dielectric material at p-polarization, wherein said means for directing an x-ray pulse is adapted to provide sufficient energy to alter the Brewster's angle reflectivity of said dielectric material at said wavelength $\lambda_1$, wherein said p-polarized probe beam is directed at said wavelength $\lambda_1$ at Brewster's angle of incidence onto said area of said dielectric material as said reflectivity changes to produce said reflected beam.

13. The apparatus of claim 11, wherein said dielectric material comprises a diamond plate.

14. The apparatus of claim 11, wherein said probe beam is spatially encoded with time-related information.

15. The apparatus of claim 11, wherein said dielectric material is oriented at an angle relative to said x-ray pulse to encode a linear gradient of arrival times on said probe beam.

16. The apparatus of claim 11, wherein said means for detecting comprises a CCD detector array onto which said reflected beam is directed.

17. The apparatus of claim 11, wherein the means for detecting comprises a film onto which said reflected beam is imaged.

18. The apparatus of claim 11, wherein said dielectric material is selected from the group consisting of z-cut alpha quartz ($SiO_2$) and z-cut sapphire ($Al_2O_3$).

19. The apparatus of claim 11, further comprising a transmitted beam that comprises the reciprocal intensity of said reflected beam, wherein both said transmitted beam and said reflected beam comprises time-varying reflectivity information.

20. The apparatus of claim 11, wherein said dielectric material comprises an antireflection coating.

* * * * *